Aug. 7, 1962 G. B. BARSTOW Plant Pat. 2,160
SETCREASEA PURPUREA
Filed May 5, 1959
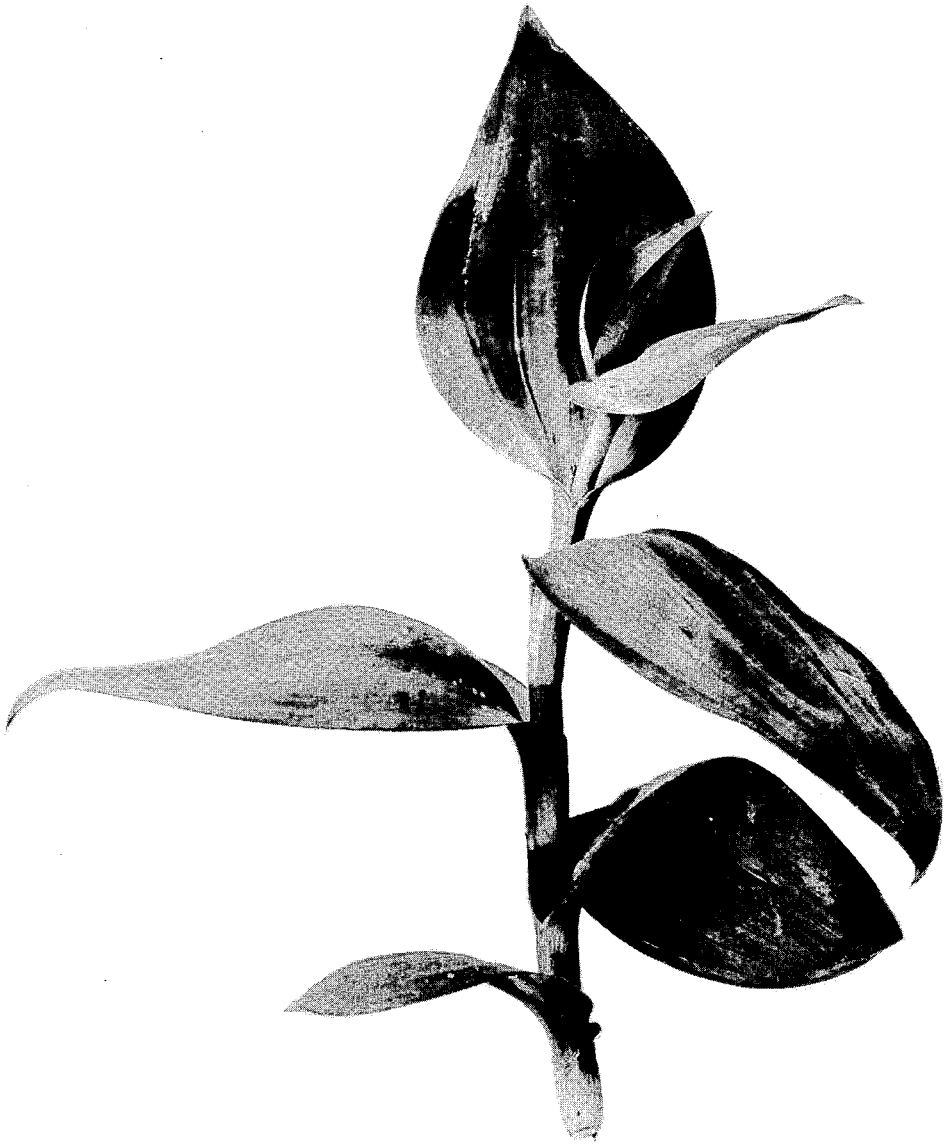

United States Patent Office

Plant Pat. 2,160
Patented Aug. 7, 1962

2,160
SETCREASEA PURPUREA
George Baham Barstow, Torrance, Calif.
Filed May 5, 1959, Ser. No. 811,241
1 Claim. (Cl. 47—59)

This invention relates to improvements in the ornamental plant *Setcreasea purpurea* and a new and distinct variety of said plant. The new variety is a mutation occurring and discovered December, 4, 1958, in applicant's greenhouse. Three hundred of the original species plant were growing in this greenhouse and on the date given one plant was discovered to have become sport. This plant was located in the southwest corner of the greenhouse, but completely surrounded by plants of the original species. The greenhouse is a glassed-in hothouse type and the plants were growing in metal containers. The greenhouse was located at 1510 West Carson Street, Torrance, California.

Asexual propagation of the newly discovered plant was made at Los Angeles, California by cuttings. The cuttings have consistently produced the new type hereinafter described. The accompanying illustration shows a typical plant of the new variety. The original species from which the present plant was derived as described by F. J. Hermann in Baileya, Volume 5, Number 4, page 151, 1957, is as follows:

"Setcreasea purpurea

"Stems, leaves, and involucral bracts succulent and rather rigged, suffused with deep violet purple, the only green apparent being on the upper surface of the leaf blades toward the base and in the thin, membranaceous bracteoles; roots fibrous; stems stout, 35 cm. high, 5–6 mm. in diameter, sub-erect or ascending, simple or occasionally branched; internodes 2–10 cm. long; leaves 3–16 cm. long 'the lower 3–7 cm. long, the middle to 16 cm., the upper 8–9 cm.', 2½–3 cm. wide, diviricate or drooping, broadly oblong lanceolate, rather abruptly acute, gradually narrowed to the sheathing base, the blades thick, glabrous below, very sparsely pilose above, the margin entire, short ciliate and sparsely long pilose, the sheaths 7–10 mm. long, the lower, at least, sparsely, pilose without, the margin densely pilose at the U-shaped mouth; inflorescence a pair of terminal fascicles of 9–16 subsessile flowers subtended by 1 or 2 foliaceous, conduplicate involucral bracts 5–8 cm. long, 3–4 cm. wide, the floral bracts 10–12 mm. long, broadly ovate, abruptly acute, white hyaline and membranous; pedicels 3 mm. long 'elongation in flute to 6 mm.', white translucent, the upper ⅔ long villous with white ascending hairs 4 mm. long; sepals erect, 9 mm. long, 2½ mm. wide at the middle, narrowly oblong, hyaline, flushed with green especially along the mid-rib, about half the length of the petals, sparsely villous at the base without, otherwise glabrous, petals 17 mm. long, 11 mm. wide at the center, rhomboid, distinctly clawed, 'the clawes evidently weakly coalescent for 1–2 mm. at the base,' bright pink within, whitish pink without; stamens 15–17 mm. long, inserted in pairs near the base of the petals; filaments deep pink 'white below the anther,' with 10–12 divergent multicellular hairs '2–3 mm. long' midway above the base; anthers versatile, .75 mm. long, 2 mm. wide, the orange yellow connective 1½ mm. wide; style 12 mm. long, pink 'white below the stigma'; stigma flattish bluntly trilobed."

The present plant differs from this original species in that the new variety is of gigantic proportions when compared with the original species when the two types are grown under similar environmental conditions. The stems, leaves and bracts of the new variety attain a size in the order of two or more times as great as the size of the corresponding organs of the original species. The new variety attains height greater than the original species and is more nearly upright in habit of growth than is the species when the two types are grown under similar environmental circumstances. Stems of the new variety grow to 10 mm. in diameter. The leaves are 6 to 8.5 cm. wide. The blades are broadly ovate, reflexed and convex. The sheaths grow to 20 mm. long and the involucral bracts to 12 cm. long and 7 cm. wide. The pedicels in flower are up to 10 mm. long.

I claim:

The new and distinct variety of *Setcreasea purpurea* plant substantially as herein described and illustrated.

No references cited.